US00PP22142P2

(12) United States Plant Patent
Podaras

(10) Patent No.: US PP22,142 P2
(45) Date of Patent: Sep. 13, 2011

(54) ***BUDDLEJA* PLANT NAMED 'PODARAS #6'**

(50) Latin Name: ***Buddleja davidii*×*Buddleja alternifolia***
Varietal Denomination: 'Podaras #6'

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,660

(22) Filed: Mar. 2, 2010

(51) Int. Cl.
*A01H 5/00* (2006.01)

(52) U.S. Cl. ..... Plt./242

(58) Field of Classification Search ..... Plt./242
See application file for complete search history.

*Primary Examiner* — Susan McCormick Ewoldt
(74) *Attorney, Agent, or Firm* — C. A. Whealy

(57) ABSTRACT

A new and distinct cultivar of *Buddleja* plant named 'Podaras #6', characterized by its compact, upright and outwardly spreading plant habit; freely flowering habit; sterile light violet-colored flowers; and good garden performance.

1 Drawing Sheet

Botanical designation: *Buddleja davidii*×*Buddleja alternifolia.*

Cultivar denomination: 'PODARAS #6'.

BACKGROUND OF THE INVENTION

The present invention relates to a new and distinct cultivar of *Buddleja* plant, botanically known as *Buddleja davidii*× *Buddleja alternifolia* and hereinafter referred to by the name 'Podaras #6'.

The new *Buddleja* plant is a product of a planned breeding program conducted by the Inventor in Ithaca, N.Y. The objective of the breeding program was to create new compact and sterile *Buddleja* plants with unique and attractive flower coloration.

The new *Buddleja* plant originated from a cross-pollination on Mar. 7, 2007 in Ithaca, N.Y., of two unnamed selections of *Buddleja davidii*×*Buddleja alternifolia*, not patented. The new *Buddleja* plant was discovered and selected by the Inventor as a single flowering plant within the progeny of the stated cross-pollination in a controlled environment in Ithaca, N.Y. in August, 2007.

Asexual reproduction of the new *Buddleja* plant by cuttings in a controlled greenhouse environment in West Chicago, Ill. since February, 2008, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras #6'. These characteristics in combination distinguish 'Podaras #6' as a new and distinct *Buddleja* plant:

1. Compact, upright and outwardly spreading plant habit.
2. Freely flowering habit.
3. Sterile light violet-colored flowers.
4. Good garden performance.

Plants of the new *Buddleja* differ from plants of the parent selections primarily in growth habit as plants of the new *Buddleja* are more compact and denser than plants of the parent selections.

Plants of the new *Buddleja* can be compared to plants of *Buddleja davidii* 'Pink Delight', not patented. In side-by-side comparisons, plants of the new *Buddleja* and 'Pink Delight' differed in the following characteristics:

1. Plants of the new *Buddleja* were more compact and denser than plants of 'Pink Delight'.
2. Plants of the new *Buddleja* and 'Pink Delight' differed in leaf color as plants of 'Pink Delight' had silvery-colored leaves.
3. Flowers of plants of the new *Buddleja* were darker pink in color than flowers of plants of 'Pink Delight'.

BRIEF DESCRIPTION OF THE PHOTOGRAPHS

The accompanying colored photographs illustrate the overall appearance of the new *Buddleja* plant, showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Podaras #6' grown in a container.

The photograph at the top of the sheet is a close-up view of a typical inflorescence of 'Podaras #6'.

DETAILED BOTANICAL DESCRIPTION

The aforementioned photographs and following observations, measurements and values describe plants grown in Arroyo Grande, Calif. under commercial practice during the summer in 12.5-cm containers in a polyethylene-covered greenhouse with day temperatures averaging 21° C. and night temperatures averaging 7° C. Plants were pinched two times and were one year old when the photographs and description were taken. In the following description, color references are made to The Royal Horticultural Society Colour Chart, 2007 Edition, except where general terms of ordinary dictionary significance are used.

Botanical classification: *Buddleja davidii*×*Buddleja alternifolia* 'Podaras #6'.

Parentage:

*Female, or seed, parent.*—Unnamed selection of *Buddleja davidii*×*Buddleja alternifolia*, not patented.

*Male, or pollen, parent.*—Unnamed selection of *Buddleja davidii*×*Buddleja alternifolia*, not patented.

Propagation:

*Type.*—By cuttings.

*Time to initiate roots plant, summer.*—About two weeks at temperatures of 18° C. to 24° C.

*Time to initiate roots plant, winter.*—About two to three weeks at temperatures of 18° C. to 24° C.

*Time to produce a rooted plant, summer.*—About three weeks at temperatures of 18° C. to 24° C.

*Time to produce a rooted plant, winter.*—About three to four weeks at temperatures of 18° C. to 24° C.

*Root description.*—Fibrous, fine; white in color.

*Rooting habit.*—Freely branching; moderately dense.

Plant description:

*Plant form/habit.*—Deciduous perennial shrub; compact, upright and outwardly spreading plant habit; broad inverted triangle; vigorous growth habit.

*Plant height.*—About 28 cm.

*Plant width* (*spread*).—About 42 cm by 46 cm.

*Lateral branches.*—Quantity: About ten main branches per plant. Length: About 29 cm. Diameter: About 6 mm. Internode length: About 2 cm to 2.5 cm. Strength: Strong. Texture, developing stems: Lanulose. Texture, mature stems: Smooth, glabrous. Color, developing: Close to 193C. Color, mature: Close to 199A to 199B.

Foliage description:

*Arrangement.*—Opposite, simple.

*Length.*—About 5.5 cm.

*Width.*—About 1.7 cm.

*Shape.*—Elliptical.

*Apex.*—Acute.

*Base.*—Attenuate.

*Margin.*—Serrulate to crenate.

*Texture, upper surface.*—Smooth, glabrous.

*Texture, lower surface.*—Lanulose.

*Venation pattern.*—Pinnate, reticulate.

*Color.*—Developing leaves, upper surface: Close to 146A. Developing leaves, lower surface: Close to 191C. Fully expanded leaves, upper surface: Close to 146A; venation, close to 137A. Fully expanded leaves, lower surface: Close to 147C; venation, close to 148B.

*Petiole.*—Length: About 4 mm. Diameter: About 1.5 mm. Texture, upper and lower surfaces: Pubescent. Color, upper and lower surfaces: Close to 146C.

Flower description:

*Flower type/habit.*—Single rotate and salverform flowers arranged in compound terminal and axillary panicles; flowers face upright and outward; panicles roughly conical in shape; freely flowering habit with about 130 flower buds and flowers developing per inflorescence.

*Fragrance.*—Faint, sweet.

*Natural flowering season.*—Plants begin flowering about three months after planting; flowering continuous from spring until frost in California.

*Postproduction longevity.*—Flowers last about three to four days on the plant; flowers persistent.

*Flower buds.*—Height: About 1.3 cm. Diameter: About 3 mm. Shape: Oblong. Color: Close to N88D.

*Inflorescence height.*—About 6.3 cm.

*Inflorescence diameter.*—About 3.6 cm.

*Flower diameter.*—About 9 mm.

*Flower depth.*—About 1.5 cm.

*Flower throat, diameter.*—About 2 mm.

*Flower tube, length.*—About 9 mm.

*Flower tube, diameter at base.*—About 2 mm.

*Petals.*—Quantity per flower: Typically four in a single whorl; petals fused into a narrow tube. Lobe length: About 4 mm. Lobe width: About 4 mm. Lobe shape: Roughly spatulate. Lobe apex: Rounded. Lobe margin: Minutely erose, crinkled. Texture, upper and lower lobe surfaces: Smooth, glabrous. Texture, throat: Slightly pubescent. Texture, tube: Smooth, glabrous. Color: Developing petals, upper surface: Close to 86C. Developing petals, lower surface: Close to N88D. Fully expanded petals, upper surface: Close to 86D; venation, close to 86D. Fully expanded petals, lower surface: Close to N88C to N88D; venation, close to N88C. Throat: Close to N170A; venation, close to N170A. Tube: Close to 183D; venation, close to 183D.

*Sepals.*—Quantity per flower: Typically four in a single whorl, fused towards the base; campanulate calyx. Length: About 2 mm. Width: About 1 mm. Shape: Lanceolate. Apex: Acute. Margin: Entire. Texture, upper surface: Smooth, glabrous. Texture, lower surface: Pubescent. Color, upper surface: Close to 138A. Color, lower surface: Close to 147C.

*Peduncles.*—Length: About 1.5 cm. Diameter: About 1.5 mm. Angle: Erect to about 45° from vertical. Strength: Strong. Texture: Lanulose. Color: Close to 194B.

*Pedicels.*—Length: About 3.5 mm. Diameter: About 1 mm. Angle: About 45° from peduncle axis. Strength: Strong. Texture: Lanulose. Color: Close to 194B.

*Reproductive organs.*—Stamens: Quantity per flower: Typically four; filaments adnate to the corolla tube. Filament length: About 1.5 mm. Filament color: Close to N170A. Anther shape: Lanceolate. Anther length: About 1 mm. Anther color: Close to 155A. Pollen amount: None. Pistils: Quantity per flower: One. Pistil length: About 5 mm. Stigma shape: Oval. Stigma color: Close to 138A. Style length: About 2 mm. Style color: Close to 138B. Ovary color: Close to 145A.

*Seed/fruit.*—Flowers of plants of the new *Buddleja* are sterile and seed and fruit development have not been observed.

Disease/pest resistance: Plants of the new *Buddleja* have been not been observed to be resistant to pathogens and pests common to *Buddleja*.

Garden performance: Plants of the new *Buddleja* have been observed to have good garden performance and tolerate rain, wind and temperatures ranging from about 0° C. to about 40° C.

It is claimed:

1. A new and distinct *Buddleja* plant named 'Podaras #6' as illustrated and described.

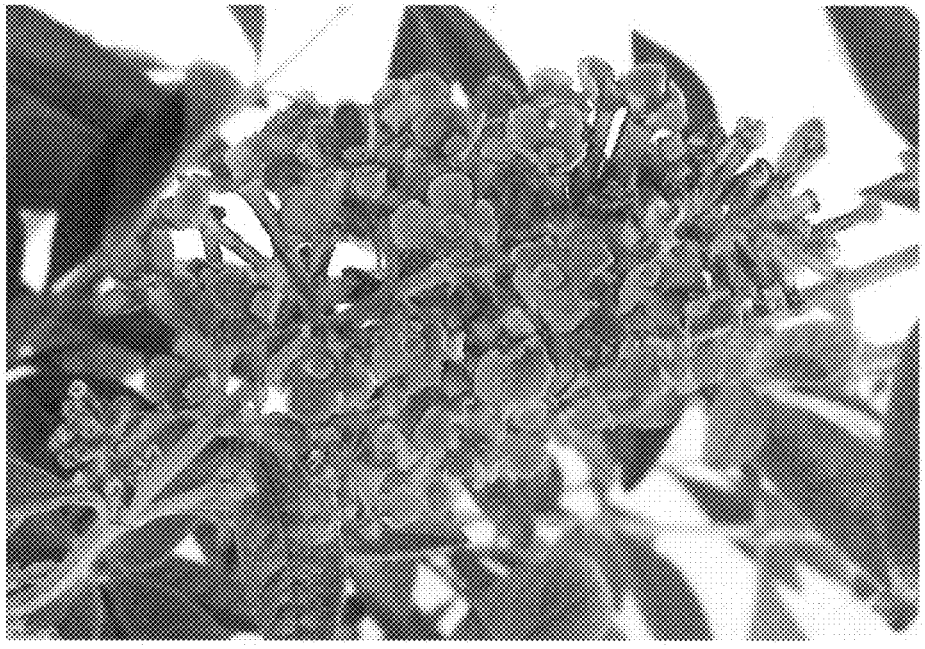
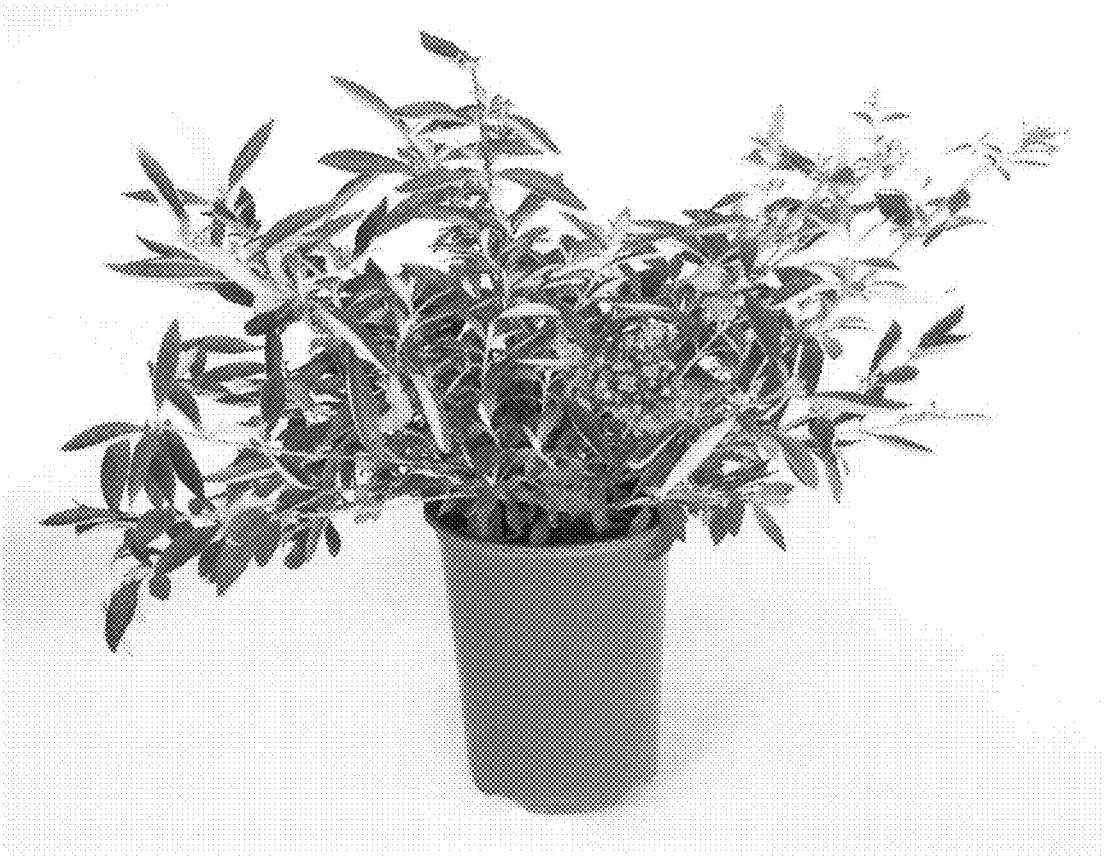

* * * * *